(12) United States Patent
Eh

(10) Patent No.: US 7,368,613 B2
(45) Date of Patent: May 6, 2008

(54) SANDAL FRAGRANCES

(75) Inventor: Marcus Eh, Holzminden (DE)

(73) Assignee: Symrise GmbH & Co. KG, Holzminden (DE)

( * ) Notice: Subject to any disclaimer, the term of this patent is extended or adjusted under 35 U.S.C. 154(b) by 0 days.

(21) Appl. No.: 11/422,917

(22) Filed: Jun. 8, 2006

(65) Prior Publication Data
US 2006/0281648 A1    Dec. 14, 2006

(30) Foreign Application Priority Data
Jun. 10, 2005  (DE)  ........................ 10 2005 026 801

(51) Int. Cl.
C07C 27/10   (2006.01)
C07C 29/10   (2006.01)
C07C 35/00   (2006.01)
C07C 35/21   (2006.01)

(52) U.S. Cl. ...................................... 568/700; 568/816

(58) Field of Classification Search .................... None
See application file for complete search history.

(56) References Cited

U.S. PATENT DOCUMENTS
5,189,013 A    2/1993   Chapuis

FOREIGN PATENT DOCUMENTS
EP    0 373 556    6/1990

OTHER PUBLICATIONS
Berthiol et al (Tetrahedron Leters (2003), 44,(6), 1221-1225).*

* cited by examiner

Primary Examiner—Samuel Barts
Assistant Examiner—Kellette Gale
(74) Attorney, Agent, or Firm—Roylance, Abrams, Berdo & Goodman, L.L.P.

(57) ABSTRACT

A compound of formula (Ia) or (Ib),

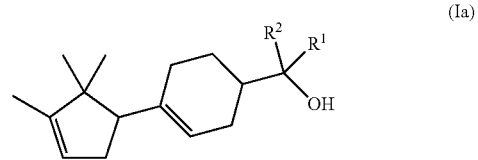

(Ia)

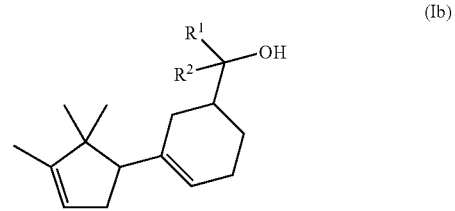

(Ib)

wherein in each of formulae (Ia) and (Ib) $R^1$ and $R^2$, independently of one another, are H or $CH_3$, and the use thereof as a sandalwood fragrance.

12 Claims, No Drawings

SANDAL FRAGRANCES

The present invention relates to novel 4-(2,2,3-trimethyl-cyclopent-3-enyl)-cyclohex-3-enylalkanols (see formula (Ia) hereinbelow) and 3-(2,2,3-trimethyl-cyclopent-3-enyl)-cyclohex-3-enylalkanols (see formula (Ib) hereinbelow). The invention relates also to mixtures comprising the compounds according to the invention, to the use of a compound or mixture according to the invention as a fragrance, and to corresponding perfumed products. Finally, the invention relates also to processes for the preparation of the compounds and mixtures according to the invention and to particular intermediates which are used in the preparation processes according to the invention.

In the fragrances industry there is a lasting interest in the development of novel fragrances in order to permit the creation of new perfume oils for alcoholic and functional perfumery. Compounds having a woody odour are indispensable components in the fragrances industry. A particularly valuable class of such woody fragrances are compounds having a sandalwood odour. Structurally, compounds having a sandalwood odour are frequently distinguished by a 4-(2,2,3-trimethyl-cyclopent-3-enyl)-butan-1-ol basic structure, it being possible for the butan-1-ol side chain to be saturated or monounsaturated as well as mono- or poly-methyl-substituted. Some representatives of this class of fragrances are 2-methyl-4-(2,2,3-trimethyl-cyclopent-3-enyl)-butan-1-ol (II) (Brahmanol®, Symrise GmbH & Co. KG), 2-ethyl-4-(2,2,3-trimethyl-cyclopent-3-enyl)-but-2-en-1-ol (III) (Sandranol®, Symrise GmbH & Co. KG), 3-methyl-5-(2,2,3-trimethyl-cyclopent-3-enyl)-pent-4-en-2-ol (IV) (Ebanol®, Givaudan S.A.) and 3,3-dimethyl-5-(2,2,3-trimethyl-cyclopent-3-enyl)-pent-4-en-2-ol (V) (Polysantol®, Firmenich S.A.).

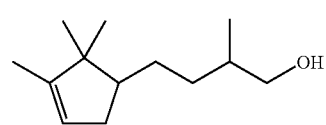
(II)

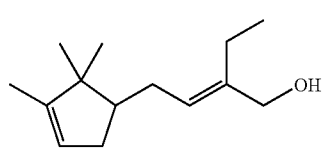
(III)

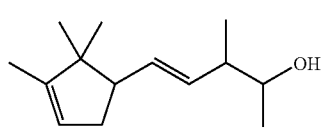
(IV)

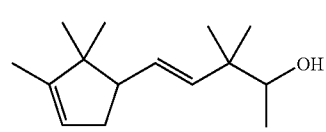
(V)

The compounds (II) to (V) shown here are distinguished by a strong sandalwood odour which varies between the individual compounds (II)-(V) in terms of (a) strength and (b) further odour-related aspects.

U.S. Pat. No. 5,189,013 discloses compounds of type (VI), that is to say compounds in which a saturated or unsaturated cyclohexanone or cyclohexanol ring is present instead of an alkanol or alkenol side chain (as in compounds (II) to (V)).

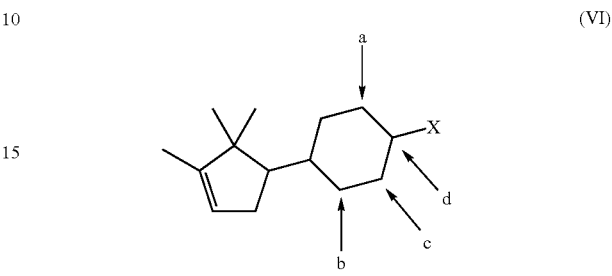
(VI)

In formula (VI), the exocyclic broken line represents a single bond (in which case X is OH) or a double bond (in which case X is O). The six-membered ring can possess one or more methyl substituents at positions a, b, c and d. Most of the compounds disclosed in U.S. Pat. No. 5,189,013 have at best a weak sandalwood odour. Only the compound 1,2-dimethyl-4-(2',2',3'-trimethyl-3'-cyclopenten-1'-yl)-2-cyclohexen-1-ol is said to have an odour whose character is similar to that of natural sandalwood. The mentioned compound is a compound of formula (VI) in which X represents OH and in which the six-membered ring possesses a double bond in the 2-position, that is to say between arrows c and b.

In Chemistry & Biodiversity, 1, 980-1021, 2004, compounds of type (VII) and (VIII) are described.

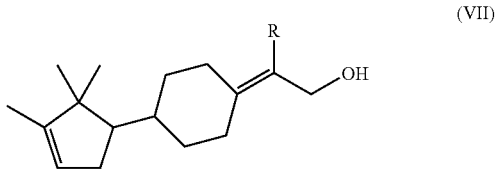
(VII)

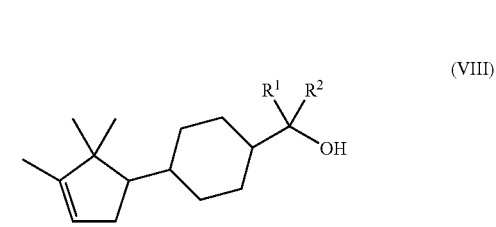
(VIII)

In the above formulae, the radicals R, $R^1$ and $R^2$ may be H or —$CH_3$. However, the disclosed compounds do not have a typical sandalwood odour in any case; if a sandalwood odour is present, it is weak and/or overlaid with other odour notes.

The object of the present invention was to provide further sandalwood fragrances, the fragrances preferably having positive secondary properties. Advantageously, the sandalwood fragrances to be provided should be distinguished by their strength and intensity as well as by high diffusivity, so that noticeable effects can still be achieved even at low doses.

This object is achieved according to the invention by a compound of formula (Ia) or (Ib)

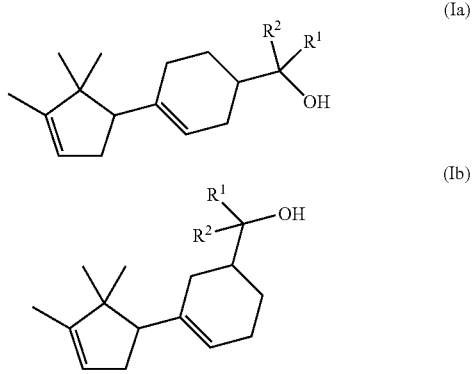

wherein in each of formulae (Ia) and (Ib) $R^1$ and $R^2$, independently of one another, are H or $CH_3$.

The compound according to the invention can be present in particular in the form of
(a) a pure optically active enantiomer,
(b) a racemic mixture of different enantiomers of the diastereoisomeric enantiomer pairs, or
(c) an optically active mixture of different enantiomers.

If the substituents $R^1$ and $R^2$ are different, the compounds of formulae (Ia) and (Ib) have three chiral centres, so that four diastereoisomeric enantiomer pairs exist. If $R^1$ and $R^2$ in formulae (Ia) and (Ib) are identical, then there are only two chiral centres and consequently only two diastereoisomeric enantiomer pairs.

The compounds of formulae (Ia) and (Ib) according to the invention have a sandalwood odour that is valuable in perfumery and, furthermore, they are distinguished by the desired secondary properties (see above). In particular, the compounds of formulae (Ia) and (Ib), as well as having a very intense sandalwood note, also have particularly high diffusivity and tremendous substantivity. This is surprising in the light of the disclosure of U.S. Pat. No. 5,189,013 because, according to that publication, compounds having a double bond at the 3-position have at best a very weak sandalwood odour (see the last three entries in Table I of U.S. Pat. No. 5,189,013). Apparently, the hydroxyalkyl function —$CHR^1R^2OH$ present in the compounds of formulae (Ia) and (Ib) is responsible for the fact that, unlike the compounds disclosed in U.S. Pat. No. 5,189,013 having a double bond at the 3-position, the compounds according to the invention possess a pronounced, typical sandalwood odour. However, a corresponding reference is not to be found either in U.S. Pat. No. 5,189,013 or in Chemistry & Biodiversity, 1, 980-1021, 2004.

Compounds of formulae (Ia) and (Ib) according to the invention wherein $R^1$ is $CH_3$ and $R^2$ is H are particularly valuable in sensory terms.

The compound of formula (Ia) wherein $R^1=CH_3$ and $R^2=H$ is extraordinarily valuable. This compound has a very intense natural sandalwood note, coupled with surprisingly high diffusivity and substantivity (see Example 1.3). The corresponding compound of formula (Ib) has a slightly softer sandalwood odour.

According to a further aspect, the present invention relates also to mixtures that consist of at least one compound of formula (Ia) according to the invention and one compound of formula (Ib) according to the invention or that comprise at least one of each of those compounds. In the mixtures according to the invention, the very intense natural sandalwood odour of the compounds of formula (Ia) is uniquely coupled with the pleasant softness of the compounds of formula (Ib) to produce an unmistakable, complex and very intense sandalwood odour. With regard to the use of the preferred compounds of formulae (Ia) and (Ib) in a mixture according to the invention, the comments made above apply correspondingly.

As will be described in greater detail hereinbelow (see the synthesis route according to Scheme 1), the mixtures of compounds of formulae (Ia) and (Ib) according to the invention can be synthesised particularly economically.

The mixtures according to the invention comprise or (preferably) consist of one or more pairs of compounds of formulae (Ia) and (Ib), wherein in the pair(s) the substituents $R^1$ and $R^2$ in the compound of formula (Ia) have the same meaning as in the compound of formula (Ib).

Particular preference is given to a mixture according to the invention comprising or (preferably) consisting of a pair of compounds of formulae (Ia) and (Ib) wherein both in the compound of formula (Ia) and in the compound of formula (Ib) $R^1$ is $CH_3$ and $R^2$ is H (see Example 1 below).

The invention relates also to the use of a compound according to the invention or of a mixture according to the invention as a fragrance, the comments made above applying correspondingly with regard to preferred compounds and mixtures.

The invention relates also to a corresponding fragrance mixture having a sandalwood odour, comprising a compound according to the invention or a mixture according to the invention as well as, preferably, one or further conventional constituents (not according to the invention), such as solvents, further fragrances or the like. With regard to the preferred choice of compounds and mixture according to the invention, the comments made above of course apply correspondingly.

The invention additionally relates to perfumed products comprising a fragrance mixture according to the invention as well as a carrier or substrate which is in direct contact with the fragrance mixture. The perfumed product can advantageously be selected from the group consisting of alcoholic perfumes, personal hygiene products, and cleaning or care products for domestic use.

According to a related aspect, the invention relates further to a method of producing, enhancing or modifying a sandalwood odour in a mixture, comprising the following steps:
provision of a compound according to the invention or of a mixture according to the invention,
provision of a composition of other constituents and
mixing of the composition of other constituents with an amount of the compound according to the invention or of the mixture according to the invention that is sufficient (a) to produce a sandalwood odour in the resulting total mixture, (b) to enhance an existing sandalwood odour in the composition of other constituents or (c) to modify an existing sandalwood odour in the composition of other constituents.

The compounds of formulae (Ia) and (Ib) according to the invention can be used as individual substances or in the form of mixtures (see above) in a large number of fragrance mixtures and perfumed products. The compounds according to the invention of the formulae indicated above and the mixtures according to the invention can particularly advantageously be combined with other fragrances to form new types of perfume compositions.

By using the compounds or mixtures according to the invention of the formulae indicated above, it is possible, even with a small dose, to achieve in the resulting perfume compositions (fragrance mixtures) sandalwood notes that are very clearly reminiscent of sandalwood oil, the overall odour impression being noticeably harmonised, the radiance being increased perceptibly and the fixing, that is to say the adhering power, of the perfume composition being markedly enhanced.

Examples of fragrances with which the sandalwood fragrances of formulae (Ia) and (Ib) according to the invention can advantageously be combined are to be found, for example, in K. Bauer, D. Garbe and H. Surburg, Common Fragrance and Flavor Materials, 3$^{rd}$ Ed., Wiley-VCH, Weinheim 1997.

The following may be mentioned specifically:

extracts from natural raw materials such as essential oils, concretes, absolutes, resins, resinoids, balsams, tinctures, such as, for example, amber tincture; amyris oil; angelica seed oil; angelica root oil; aniseed oil; valerian oil; basil oil; tree moss absolute; bay oil; artemisia oil; benzoin resin; bergamot oil; beeswax absolute; birch tar oil; bitter almond oil; summer savory oil; buchu oil; cabreuva oil; oil of cade; calamus oil; camphor oil; cananga oil; cardamom oil; cascarilla oil; oil of cassia; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill oil; dill seed oil; eau de brouts absolute; oak moss absolute; elemi oil; tarragon oil; Eucalyptus citriodora oil; eucalyptus oil; fennel oil; spruce-needle oil; galbanum oil; galbanum resin; geranium oil; grapefruit oil; guaiacwood oil; gurjun balsam; gurjun balsam oil; helichrysum absolute; helichrysum oil; ginger oil; orris root absolute; orris root oil; jasmine absolute; calamus oil; blue camomile oil; Roman camomile oil; carrot seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linaloa oil; litseacubeba oil; oil of laurel leaves; oil of mace; marjoram oil; mandarin oil; massoia bark oil; mimosa absolute; musk seed oil; musk tincture; oil of clary sage; nutmeg oil; myrrh absolute; myrrh oil; myrtle oil; clove leaf oil; clove flower oil; Neroli oil; olibanum absolute; olibanum oil; opopanax oil; orange blossom absolute; orange oil; origanum oil; palmarosa oil; patchouli oil; perilla oil; Peru balsam oil; parsley leaf oil; parsley seed oil; oil of petitgrain; peppermint oil; pepper oil; pimento oil; pine oil; poley oil; rose absolute; rosewood oil; rose oil; rosemary oil; oil of Dalmatian sage; oil of Spanish sage; sandalwood oil; celery seed oil; spike oil; star anise oil; styrax oil; tagetes oil; fir-needle oil; tea tree oil; terpentine oil; thyme oil; tolu balsam; tonka absolute; tuberose absolute; vanilla extract; violet leaf absolute; verbena oil; vetiver oil; oil of juniper berries; grapeseed oil; vermouth oil; oil of wintergreen; ylang oil; oil of hyssop; civet absolute; cinnamon leaf oil; cinnamon bark oil as well as fractions thereof, or ingredients isolated therefrom;

individual fragrances from the group of the hydrocarbons, such as, for example, 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene;

of the aliphatic alcohols, such as, for example, hexanol; octanol; 3-octanol; 2,6-dimethylheptanol; 2-methylheptanol; 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; of the aliphatic aldehydes and their 1,4-dioxacycloalken-2-ones, such as, for example, hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanaldiethylacetal; 1,1-dimethoxy-2,2,5-trimethyl-4-hexene; citronellyloxyacetaldehyde;

of the aliphatic ketones and their oximes, such as, for example, 2-heptanone; 2-octanone; 3-octanone; 2-nonanone; 5-methyl-3-heptanone; 5-methyl-3-heptanoneoxime; 2,4,4,7-tetramethyl-6-octen-3-one; of the aliphatic sulfur-containing compounds, such as, for example, 3-methylthio-hexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of the aliphatic nitriles, such as, for example, 2-nonenoic acid nitrile; 2-tridecenoic acid nitrile; 2,12-tridecenoic acid nitrile; 3,7-dimethyl-2,6-octadienoic acid nitrile; 3,7-dimethyl-6-octenoic acid nitrile;

of the aliphatic carboxylic acids and their esters, such as, for example, (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxyacetate; methyl 3,7-dimethyl-2,6-octadienoate;

of the acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and their formates, acetates, propionates, isobutyrates, butyrates, isovalerates, pentanoates, hexanoates, crotonates, tiglinates, 3-methyl-2-butenoates;

of the acyclic terpenealdehydes and ketones, such as, for example, geranial; neral; citronellal; 7-hydroxy-3,7-dimethyloctanal; 7-methoxy-3,7-dimethyloctanal; 2,6,10-trimethyl-9-undecenal; geranylacetone; and the dimethyl- and diethyl-acetals of geranial, neral, 7-hydroxy-3,7-dimethyloctanal;

of the cyclic terpene alcohols, such as, for example, menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and their formates, acetates, propionates, isobutyrates, butyrates, isovalerates, pentanoates, hexanoates, crotonates, tiglinates, 3-methyl-2-butenoates;

of the cyclic terpenealdehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootcatone; dihydronootcatone; alpha-sinensal; beta-sinensal; acetylated cedar wood oil (methyl cedryl ketone);

of the cyclic alcohols, such as, for example, 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of the cycloaliphatic alcohols, such as, for example, alpha-3,3-trimethylcyclohexylmethanol; 2-methyl-4-(2,2,3-trimethyl-3-cyclopent-1-yl)-butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of the cyclic and cycloaliphatic ethers, such as, for example, cineol; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyl-dodecahydronaphtho[2,1-b]furan; 1,5,9-trimethyl-13-oxabicyclo[10.1.0]-trideca-4,8-diene; rose oxide; 2-(2,4-dimethyl-3-cyclohexen-1-yl)-5-methyl-5-(1-methylpropyl)-1,3-dioxane;

of the cyclic ketones, such as, for example, 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopenta-decanone; 4-(1-ethoxyvinyl)-3,3,5,5-tetramethylcyclohexanone; 4-tert.-pentyl-cyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cyclo-heptadecen-1-one; cyclopentadecanone;

of the cycloaliphatic aldehydes, such as, for example, 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

of the cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetra-methyl-1,2,3,4,5,6,7,8-octahydro-2-naphthalenyl methyl ketone; methyl 2,6,10-trimethyl-2,5,9-cyclododecatrienyl ketone; tert.-butyl (2,4-dimethyl-3-cyclohexen-1-yl) ketone;

of the esters of cyclic alcohols, such as, for example, 2-tert-butyl cyclohexylacetate; 4-tert-butyl cyclohexylacetate; 2-tert-pentyl cyclohexylacetate; 4-tert-pentyl cyclohexylacetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

of the esters of cycloaliphatic carboxylic acids, such as, for example, allyl 3-cyclohexylpropionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolan-2-acetate;

of the aromatic hydrocarbons, such as, for example, styrene and diphenylmethane;

of the araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

of the esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; of the araliphatic ethers, such as, for example, 2-phenylethyl methyl ether; 2-phenylethyl isoamyl ether; 2-phenylethyl 1-ethoxyethyl ether; phenylacetaldehydedimethylacetal; phenylacetaldehyde-diethylacetal; hydratropaaldehydedimethylacetal; phenylacetaldehydeglycerin-acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

of the aromatic and araliphatic aldehydes, such as, for example, benzaldehyde; phenylacetaldehyde; 3-phenylpropanal; hydratropaaldehyde; 4-methyl-benzaldehyde; 4-methylphenylacetaldehyde; 3-(4-ethylphenyl)-2,2-dimethyl-propanal; 2-methyl-3-(4-isopropylphenyl)propanal; 2-methyl-3-(4-tert.-butylphenyl)propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxy-benzaldehyde; 4-hydroxy-3-ethoxybenzaldehyde; 3,4-methylenedioxy-benzaldehyde; 3,4-dimethoxybenzaldehyde; 2-methyl-3-(4-methoxyphenyl)-propanal; 2-methyl-3-(4-methylenedioxyphenyl)propanal;

of the aromatic and araliphatic ketones, such as, for example, acetophenone; 4-methylacetophenone; 4-methoxyacetophenone; 4-tert.-butyl-2,6-dimethyl-acetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of the aromatic and araliphatic carboxylic acids and their esters, such as, for example, benzoic acid; phenylacetic acid; methyl benzoate; ethyl benzoate; hexyl benzoate; benzyl benzoate; methylphenyl acetate; ethylphenyl acetate; geranylphenyl acetate; phenylethyl-phenyl acetate; methyl cinnamate; ethyl cinnamate; benzyl cinnamate; phenylethyl cinnamate; cinnamyl cinnamate; allylphenoxy acetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

of the nitrogen-containing aromatic compounds, such as, for example, 2,4,6-trinitro-1,3-dimethyl-5-tert.-butylbenzene; 3,5-dinitro-2,6-dimethyl-4-tert.-butylacetophenone; cinnamic acid nitrile; 5-phenyl-3-methyl-2-pentenoic acid nitrile; 5-phenyl-3-methylpentanoic acid nitrile; methyl anthranilate; methyl-N-methyl anthranilate; Schiff's bases of methyl anthranilate with 7-hydroxy-3,7-dimethyloctanal, 2-methyl-3-(4-tert.-butylphenyl)propanal or 2,4-dimethyl-3-cyclohexenecarbaldehyde; 6-isopropylquinoline; 6-isobutylquinoline; 6-sec.-butylquinoline; indole; scatole; 2-methoxy-3-isopropylpyrazine; 2-isobutyl-3-methoxypyrazine;

of the phenols, phenyl ethers and phenyl esters, such as, for example, estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl) phenol; p-cresylphenyl acetate;

of the heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of the lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecane dioate; ethylene-1,13-tridecane dioate; coumarin; 2,3-dihydrocoumarin; octahydrocoumarin.

Perfume oils which contain the compounds according to the invention of the formulae indicated above can be used for perfuming in liquid form, in undiluted form or diluted with a solvent. Examples of suitable solvents therefor are ethanol, isopropanol, diethylene glycol monoethyl ether, glycerol, propylene glycol, 1,2-butylene glycol, dipropylene glycol, diethyl phthalate, triethyl citrate, isopropyl myristate, etc.

Perfume oils (fragrance mixtures) which contain compounds according to the invention can be absorbed on a carrier, which ensures both fine distribution of the fragrances in the product and controlled release during use. Such carriers can be porous inorganic materials, such as light-weight sulphate (Leichtsulfat), silica gels, zeolites, gypsums, clays, clay granules, gas concrete, etc., or organic materials, such as woods and cellulose-based substances.

Perfume oils (fragrance mixtures) which contain compounds according to the invention can also be present in microencapsulated form, in spray-dried form, as inclusion complexes or as extruded products and can be added in this form to the product to be perfumed.

The properties of the perfume oils so modified can optionally be optimised further in terms of more targeted release of the fragrance, by so-called "coating" with suitable materials, to which end wax-like plastics materials, such as, for example, polyvinyl alcohol, are preferably used.

Microencapsulation of the perfume oils can be carried out, for example, by the so-called coacervation process using capsule materials made of polyurethane-like substances or soft gelatin, for example. The spray-dried perfume oils can be prepared, for example, by spray-drying an emulsion or dispersion containing the perfume oil, it being possible to use as carriers modified starches, proteins, dextrin and plant gums. Inclusion complexes can be prepared, for example, by introducing dispersions of the perfume oil and cyclodextrin or urea derivatives into a suitable solvent, for example water. Extrusion products can be prepared by melting the perfume oils with a suitable wax-like substance and by extrusion followed by solidification, optionally in a suitable solvent, for example isopropanol.

In perfume compositions, the amount of the compounds according to the invention that is used is preferably from 0.05 to 50 wt. %, especially from 0.5 to 20 wt. %, based on the total perfume oil.

Perfume oils (fragrance mixtures) which contain compounds according to the invention can be used in concentrated form, in solutions or in above-described modified form for the preparation of, for example, perfume extracts, eau de parfums, eau de toilettes, after-shaves, eau de colognes, pre-shave products, splash colognes and perfumed freshening cloths, as well as the perfuming of acidic, alkaline and neutral cleaning agents, such as, for example, floor cleaners, window cleaners, washing-up liquids, bath and sanitary cleaners, scouring cream, solid and liquid WC cleaners, carpet cleaners in powder and foam form, liquid detergents, detergents in powder form, wash pre-treatment agents such as bleaches, soaking agents and stain removers, fabric conditioners, wash soaps, wash tablets, disinfectants, surface disinfectants, and of air fresheners in liquid form, gel form or in a form applied to a solid carrier, aerosol sprays, waxes and polishes, such as furniture polishes, floor waxes, shoe creams, as well as personal hygiene products, such as, for example, solid and liquid soaps, shower gels, shampoos, shaving soaps, shaving foams, bath oils, cosmetic emulsions of the oil-in-water, water-in-oil and water-in-oil-in-water type, such as, for example, skin creams and lotions, face creams and lotions, sun protection creams and lotions, after-sun creams and lotions, hand creams and lotions, foot creams and lotions, depilatory creams and lotions, after-shave creams and lotions, self-tanning creams and lotions, hair care products, such as, for example, hairsprays, hair gels, hair setting lotions, hair rinses, permanent and semi-permanent hair dyes, hair styling agents, such as cold-wave and hair smoothing agents, hair tonics, hair creams and lotions, deodorants and antiperspirants, such as, for example, underarm sprays, roll-ons, deodorant sticks, deodorant creams, products of decorative cosmetics, such as, for example, eye shadows, nail lacquers, make-up, lipsticks, mascara, and of candles, lamp oils, joss sticks, insecticides, repellents and propellants.

The invention relates also to a process for the preparation of a compound according to the invention or of a mixture according to the invention, comprising the following steps:

provision or preparation of a compound of formula (IXa) or (IXb)

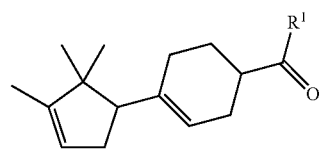

(IXa)

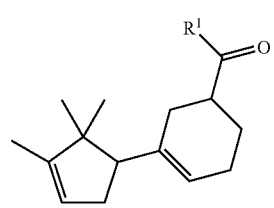

(IXb)

or of a mixture of a compound of formula (IXa) with a compound of formula (IXb), wherein $R^1$ represents H or $CH_3$, reduction of the compound or mixture so that a compound or mixture according to the invention wherein $R^2$ is H is formed, $R^1$ having the same meaning as given for the compounds of formulae (IXa) and (IXb), or nucleophilic addition of an organometallic compound of methyl anion nature to the compound or to the compounds contained in the mixture, so that a compound or mixture according to the invention wherein $R^2$ is $CH_3$ is formed, $R^1$ having the same meaning as given for the compounds of formulae (IXa) and (IXb).

The indicated compounds of formulae (IXa) and (IXb) are novel. Accordingly, the present invention relates also to the compounds of formulae (IXa) and (IXb) or the mixtures of a compound of formula (IXa) with a compound of formula (IXb), wherein $R^1$ represents H or $CH_3$.

In the process according to the invention for the preparation of the compounds of formulae (Ia) or (Ib), or of the corresponding mixtures, wherein $R^2$=H, the reduction of the compound or of the mixture (formulae (IXa) and (IXb)) is preferably carried out with a reducing agent such as sodium borohydride or lithium aluminium hydride.

For the corresponding preparation of compounds of formulae (Ia) or (Ib), or of the corresponding mixtures, wherein $R^2$=$CH_3$, the nucleophilic addition is preferably carried out by means of a Grignard reaction, for example using a methylmagnesium halide such as methylmagnesium chloride. Alternatively, methyl lithium can be used.

These processes according to the invention are particularly suitable for the preparation of a mixture of compounds of formulae (Ia) and (Ib).

For the preparation of the intermediates (which are themselves novel), that is to say of the compounds of formulae (IXa) or (IXb), or (preferably) of a mixture of a compound of formula (IXa) with a compound of formulae (IXb), wherein $R^1$ represents H or $CH_3$, the following steps are preferably carried out:

conversion of a compound of formula (X)

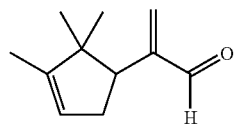

(X)

by means of an olefination reaction into a compound of formula (XI),

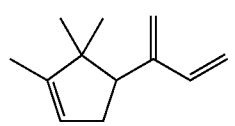

(XI)

reaction of the compound of formula (XI) with a compound of formula (XII)

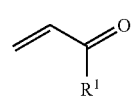

(XII)

by means of Diels-Alder reaction to give a mixture of compounds of formulae (IXa) and (IXb), wherein in formula (XII) $R^1$ has the meaning given above (for (IXa), (IXb)), and optionally separation of the compounds of formulae (IXa) and (IXb) from one another.

In the first reaction step, α-methylenecampholenealdehyde, for example, that is to say the compound (X), is reacted in a Wittig reaction with methyltriphenyl-phosphonium bromide in the presence of potassium tert-butanolate as base (Fitjer, L., Quabeck, U., Synth. Commun., 1985, 15, 855-864). Alternative olefination reactions for converting the compound of formula (X) into the compound of formula (XI) are known to the person skilled in the art.

The diene of formula (XI) obtained as a result of the first reaction step is then reacted in a Diels-Alder reaction, typically in the presence of catalytic amounts of aluminium trichloride, with the α,β-unsaturated carbonyl compound of formula (XII) in which $R^1$ has the meaning given above.

Starting from the compound of formula (X), it is possible to prepare a compound or mixture of formulae (Ia) and (Ib) in a total of three steps. Scheme 1 below illustrates the reaction steps that are to be carried out; methyl-triphenylphosphonium bromide is mentioned in Scheme 1 simply by way of example.

Scheme 1

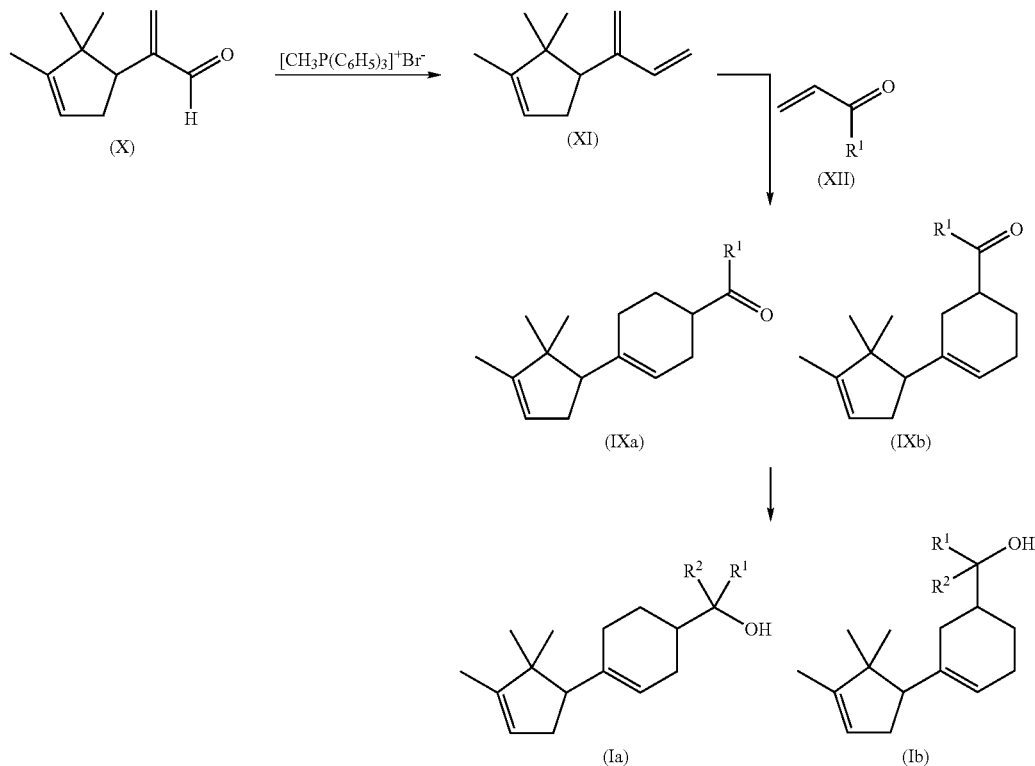

The invention relates also to a process (in so far as alternative) for the preparation of compounds of formula (Ia)

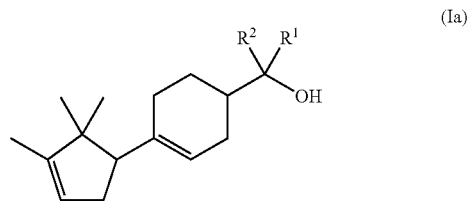

wherein $R^1$ represents H or $CH_3$ and $R^2$ represents H, comprising the following steps:

provision or preparation of a compound of formula (XIV),

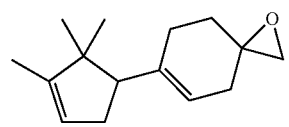

opening of the epoxide function of the compound of formula (XIV) and formation of an aldehyde of formula (IXa) wherein $R^2$=H

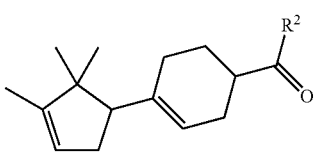

reduction of the aldehyde so that a compound of formula (Ia) wherein $R^1$, $R^2$=H is formed, or nucleophilic addition of an organometallic compound of methyl anion nature to the aldehyde, so that a compound of formula (Ia) wherein $R^1$=$CH_3$, $R^2$=H is formed.

The compound (XIV), that is to say 6-(2,2,3-trimethyl-cyclopent-3-enyl)-1-oxa-spiro[2.5]oct-5-ene, is itself novel. The present invention accordingly relates also thereto.

The opening of the epoxide function of the compound of formula (XIV) is preferably carried out in the presence of $BF_3 \cdot OEt_2$, which then leads directly to the aldehyde (XIVa). The aldehyde is then either reacted with a reducing agent, such as, for example, sodium borohydride or lithiuim aluminium hydride (for example under standard conditions), so that a compound of formula (Ia) wherein $R^1$, $R^2$=H is formed, or the nucleophilic addition of an organometallic compound of methyl anion nature to the aldehyde is carried out, for example by means of a Grignard reaction (for example under standard conditions), for example with methylmagnesium halide, preferably methylmagnesium chloride, so that a compound of formula (Ia) wherein $R^1$=$CH_3$, $R^2$=H is formed.

The compound of formula (XIV) according to the invention is a particularly suitable intermediate for the preparation of the compounds of formula (Ia) wherein $R^2$=H. A process according to the invention for the preparation of a compound of formula (XIV) according to the invention comprises the following steps:

provision or preparation of a compound of formula (XIII),

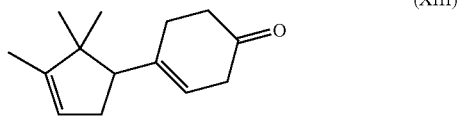

(XIII)

conversion of the carbonyl function of the compound of formula (XIII) into an epoxide function, so that the compound of formula (XIV) is obtained.

The compound of formula (XIII) is hereby converted into the epoxide of formula (XIV) preferably by reaction with trimethylsulfoxonium iodide, preferably in the presence of sodium hydride, see E. J. Corey et al., J. Am. Chem. Soc., 87, 1353-1364, 1965.

Starting from the compound of formula (XIII), it is possible to prepare a compound of formula (Ia) wherein $R^2$=H in a total of three steps. Scheme 2 below illustrates the reaction steps that are to be carried out. $BF_3 \cdot OEt_2$ is mentioned in Scheme 2 simply by way of example, although the corresponding procedure is preferred. For the rearrangement of the epoxide in the presence of $BF_3 \cdot OEt_2$ to give the aldehyde (IXa) see Y. Kita et al., Tetrahedron, 55, 4979-4998, 1999.

separated and the aqueous phase is extracted three times with diethyl ether (750 ml each time). The combined organic phases are dried, filtered off and concentrated in a rotary evaporator. The resulting crude product is taken up in pentane (500 ml) again, and the precipitate that forms is filtered off with suction. The solvent is then removed in a rotary evaporator, yielding 281.6 g of crude product (XI) having a product content of 79%. The resulting crude product is used in the next step without being purified further. For structure determination by means of spectroscopy, a small sample of the crude product is purified by flash chromatography.

$^1$H-NMR (400 MHz, CDCl$_3$): δ (ppm)=0.75 (s, 3H), 1.07 (s, 3H), 1.61 (td, J=2.1, 1.6 Hz, 3H), 2.33 (dquin, J=8.2, 2.1 Hz, 2H), 2.90 (t, J=8.2 Hz, 1H), 4.98-5.06 (m, 2H), 5.20-5.23 (m, 1H), 5.27-5.33 (m, 1H), 5.33 (dd, J=17.4, 1.3 Hz, 1H), 6.38 (ddd, J=17.4, 10.8, 0.9 Hz, 1H).

$^{13}$C-NMR (100 MHz, CDCl$_3$): δ (ppm)=12.8, 21.4, 27.0, 34.9, 47.8, 51.0, 113.0, 114.9, 121.5, 140.4, 147.2, 147.3.

1.2 1-[4-(2,2,3-Trimethyl-cyclopent-3-enyl)-cyclohex-3-enyl]-ethanone (IXa wherein $R^1$=—CH$_3$)/1-[3-(2,2,3-trimethyl-cyclopent-3-enyl)-cyclohex-3-enyl]-ethanone (IXb wherein $R^1$=—CH$_3$)

Methyl vinyl ketone (124.8 g, 1.78 mol.) dissolved in toluene (75 ml) is added dropwise to a heterogeneous Scheme 2

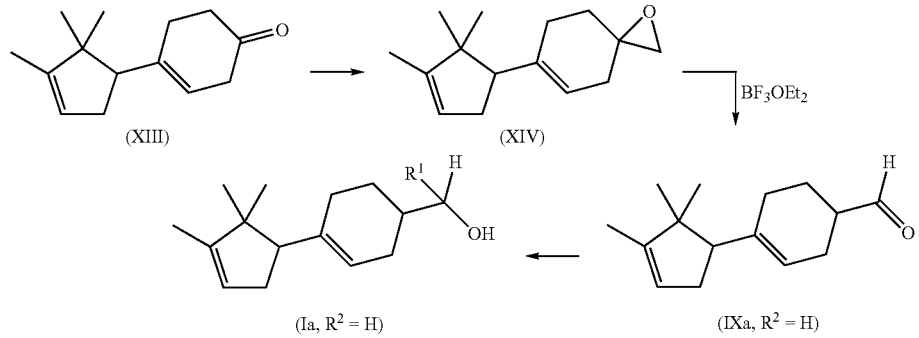

The non-limiting examples below illustrate the invention.

EXAMPLE 1

1-[4-(2,2,3-Trimethyl-cyclopent-3-enyl)-cyclohex-3-enyl]-ethanol (Ia wherein $R^1$=—CH$_3$ and $R^2$=H)/1-[3-(2,2,3-trimethyl-cyclopent-3-enyl)-cyclohex-3-enyl]-ethanol (Ib wherein $R^1$=—CH$_3$ and $R^2$=H)

1.1. 1,5,5-Trimethyl-4-(1-methylene-allyl)-cyclopentene (XI)

Potassium tert-butanolate (222.5 g, 1.98 mol.) is added to a solution of methyl-triphenylphosphonium bromide (708.1 g, 1.98 mol.) in diethyl ether (1900 ml). When the addition is complete, the yellow solution that has formed is heated to reflux temperature, and after 60 minutes α-methylenecampholenealdehyde (X, 247.4 g, 1.51 mol.) is added dropwise. When the reaction is complete, the mixture is allowed to cool to room temperature, and pentane (600 ml) and water (600 ml) are added with vigorous stirring. The resulting precipitate is filtered off with suction; the phases are then solution of aluminium chloride (23.79 g, 0.18 mol.) in toluene (350 ml) in such a manner that the temperature does not exceed 25° C. Stirring is carried out for 30 minutes, before the diene (XI, 264.0 g, 1.28 mol., 79% purity), dissolved in toluene (75 ml), is added. The mixture is then heated for 24 hours at 90° C. When the reaction is complete, the reaction mixture is added to saturated NaHCO$_3$ solution (500 ml), the phases are separated and the organic phase is washed with saturated NaHCO$_3$ solution until neutral. The organic phase is then dried over Na$_2$SO$_4$, filtered off and concentrated in a rotary evaporator. 404.1 g of crude product are obtained, the two isomers (IXa) and (IXb) wherein $R^1$=—CH$_3$ being formed in a ratio of 3:1 and in an overall purity of 73.2%. The resulting crude product is used in the next step without being purified further. For structure determination by means of spectroscopy, a small sample of the crude product is purified by flash chromatography (cyclohexane/EtOAc=10:1, R$_f$=0.24).

The spectroscopic data relate to (IXa wherein $R^1$=—CH$_3$).

$^1$H-NMR (400 MHz, CDCl$_3$): δ (ppm)=0.73 (s, 3H), 1.04 (s, 3H), 1.56-1.60 (m, 3H), 1.89-2.27 (m, 7H), 2.17 (s, 3H), 2.23-2.37 (m, 1H), 2.39-2.46 (m, 1H), 2.51-2.60 (m, 1H), 5.22-5.27 (m, 1H), 5.45-5.52 (m, 1H).

$^{13}$C-NMR (100 MHz, CDCl$_3$): δ (ppm)=12.7, 20.6, 25.1, 26.7, 27.2, 27.9, 28.7, 32.4, 47.5, 48.1, 57.3, 120.5, 121.2, 137.5, 146.9, 211.2.

Odour: weak sandalwood note, woody-sweet, mossy, nutty.

1.3 1-[4-(2,2,3-Trimethyl-cyclopent-3-enyl)-cyclohex-3-enyl]-ethanol (Ia wherein R$^1$=—CH$_3$ and R$^2$=H)/1-[3-(2,2,3-trimethyl-cyclopent-3-enyl)-cyclohex-3-enyl]-ethanol (Ib wherein R$^1$=—CH$_3$ and R$^2$=H)

Sodium borohydride (15.1 g, 0.4 mol.) is added in portions to a solution, cooled to 0° C., of the reaction mixture according to procedure 1.2 (IXa/IXb=3:1, 253.6 g, 0.80 mol., purity 73.2%) in ethanol (600 ml). When the addition is complete, the mixture is allowed to come to room temperature, and stirring is carried out for one hour. When the reaction is complete, 2M HCl is added until the reaction mixture reaches pH=7. The ethanol is then removed in a rotary evaporator, and the residue is taken up in saturated NaCl solution (300 ml). The mixture is extracted three times with diethyl ether (500 ml each time) before the combined organic phases are dried over Na$_2$SO$_4$, filtered off and concentrated in a rotary evaporator. 247.1 g of crude product are obtained, the two isomers (Ia) and (Ib) wherein R$^1$=—CH$_3$ and R$^2$=H being obtained in a ratio of 3:1 and in an overall purity of 76.5%. Subsequent vacuum distillation on a 30 cm packed column (b.p.: 100-103° C., 0.11 mbar) yields the desired sandalwood fragrance (Ia/Ib=3:1, wherein R$^1$=—CH$_3$ and R$^2$=H) in 97% purity.

The two regioisomers (Ia) and (Ib) wherein R$^1$=—CH$_3$ and R$^2$=H could be separated by preparative HPLC (column: GROM Saphir 110 Si, 5 µm, 125×20 mm; eluant: methanol/water=3:1; flow rate: 25 ml/min; pressure: 120 bar), analysed, measured by spectrometry and evaluated in terms of odour.

1-[4-(2,2,3-Trimethyl-cyclopent-3-enyl)-cyclohex-3-enyl]-ethanol (Ia wherein R$^1$=—CH$_3$ and R$^2$=H)

$^1$H-NMR (400 MHz, CDCl$_3$): δ (ppm)=0.73 (s, 3H), 1.04 (s, 3H), 1.19 (d, J=6.3 Hz, 3H), 1.25-1.38 (m, 1H), 1.54 (s, 1H, OH), 1.43-1.60 (m, 1H), 1.59 (td, J=2.4, 1.6 Hz, 3H), 1.68-2.12 (m, 5H), 2.12-2.22 (m, 1H), 2.25-2.36 (m, 1H), 2.43 (t, J=8.4 Hz, 1H), 3.57 (quint, J=6.4 Hz, 1H), 5.24-5.27 (m, 1H), 5.45-5.52 (m, 1H).

$^{13}$C-NMR (100 MHz, CDCl$_3$): δ (ppm)=12.8, 20.7, 20.8, 25.1, 26.8, 28.1, 29.5, 32.5, 41.5, 48.2, 57.6, 71.9, 121.5, 121.6, 137.8, 147.4.

Odour: very intense sandalwood note, naturally reminiscent of β-santalol, somewhat milky-fatty with slight musky character, tremendous spatial effect (diffusivity) and adhesion (substantivity).

1-[3-(2,2,3-Trimethyl-cyclopent-3-enyl)-cyclohex-3-enyl]-ethanol (Ib wherein R$^1$=—CH$_3$ and R$^2$=H)

$^1$H-NMR (400 MHz, CDCl$_3$): δ (ppm)=0.74 (s, 3H), 1.05 (s, 3H), 1.20 (d, J=6.3 Hz, 3H), 1.25-1.38 (m, 1H), 1.46-1.58 (m, 1H), 1.58-1.61 (m, 3H), 1.64-1.76 (m, 1H), 1.78-0.96 (m, 2H), 2.02-2.22 (m, 4H), 2.26-2.38 (m, 4H), 2.40-2.48 (m, 1H), 3.61 (quint, J=6.4 Hz, 1H), 5.24-5.28 (m, 1H), 5.46-5.53 (m, 1H).

$^{13}$C-NMR (100 MHz, CDCl$_3$): δ (ppm)=12.8, 20.7, 20.8, 24.4, 25.6, 26.9, 32.1, 32.5, 41.8, 48.2, 57.8, 71.7, 121.6, 122.5, 137.0, 147.4.

Odour: soft sandalwood note, dry, slightly dusty.

The odour of the isomeric mixture (Ia) and (Ib) wherein R$^1$=—CH$_3$ and R$^2$=H in a ratio of 3:1 is described as follows: very intense soft sandalwood note, naturalness reminiscent of β-santalol, with tremendous spatial effect (diffusivity) and adhesion (substantivity).

EXAMPLE 2

2-[4-(2,2,3-Trimethyl-cyclopent-3-enyl)-cyclohex-3-enyl]-propan-2-ol (Ia wherein R$^1$ and R$^2$=—CH$_3$)/ 2-[3-(2,2,3-Trimethyl-cyclopent-3-enyl)-cyclohex-3-enyl]-propan-2-ol (Ib wherein R$^1$ and R$^2$=—CH$_3$)

To a 3M methylmagnesium chloride solution in THF (15 ml, 45 mmol.) there is added dropwise (IXa)/(IXb)=3:1 wherein R$^1$=—CH$_3$ (8.21 g, 35 mmol.), dissolved in diethyl ether (10 ml), in such a manner that the temperature does not exceed 35° C. When the dropwise addition is complete, stirring is carried out for one hour at room temperature. When the reaction is complete, the reaction solution is poured into cold NH$_4$Cl solution (15 ml), the phases are separated, and the aqueous phase is extracted twice with diethyl ether (50 ml each time). The combined organic phases are washed once with saturated NaHCO$_3$ solution and saturated NaCl solution before being dried over Na$_2$SO$_4$, filtered off and concentrated in a rotary evaporator. 9.52 g of crude product are obtained, which is purified by flash chromatography (cyclohexane/EtOAc=10:1, R$_f$=0.21). (Ia)/(Ib) wherein R$^1$ and R$^2$=—CH$_3$ is obtained in a ratio of 3:1.

The spectroscopic data relate to (Ia wherein R$^1$ and R$^2$=—CH$_3$).

$^1$H-NMR (400 MHz, CDCl$_3$): δ (ppm)=0.75 (s, 3H), 1.06 (s, 3H), 1.18 (s, 3H), 1.20 (s, 3H), 1.18-1.30 (m, 1H), 1.47-1.60 (m, 1H), 1.60 (td, J=2.3, 1.7 Hz, 3H), 1.80-2.05 (m, 3H), 2.05-2.23 (m, 4H), 2.23-2.38 (m, 1H), 2.43 (t, J=8.2 Hz, 1H), 5.23-5.28 (m, 1H), 5.46-5.53 (m, 1H).

$^{13}$C-NMR (100 MHz, CDCl$_3$): δ (ppm)=12.7, 20.6, 24.1, 26.1, 26.8, 27.0, 27.1, 27.3, 30.4, 32.4, 45.2, 57.4, 72.5, 121.3, 121.6, 137.5, 147.1.

Odour: sandalwood note, slightly fatty.

EXAMPLE 3

[4-(2,2,3-Trimethyl-cyclopent-3-enyl)-cyclohex-3-enyl]-methanol (Ia wherein R$^1$ and R$^2$=H)/[3-(2,2,3-trimethyl-cyclopent-3-enyl)-cyclohex-3-enyl]-methanol (Ib wherein R$^1$ and R$^2$=H)

3.1 4-(2,2,3-Trimethyl-cyclopent-3-enyl)-cyclohex-3-enecarbaldehyde (IXa wherein R$^1$=H)/3-(2,2,3-trimethyl-cyclopent-3-enyl)-cyclohex-3-enecarbaldehyde (IXb wherein R$^1$=H)

Acrolein (47.85 g, 0.85 mol.), dissolved in toluene (275 ml), is added dropwise to a heterogeneous solution of aluminium chloride (12.11 g, 91.00 mmol.) in toluene (700 ml), in such a manner that the temperature does not exceed 25° C. Stirring is carried out for 30 minutes before the diene (XI, 143.8 g, 0.70 mol., 79% purity), dissolved in toluene (45 ml), is added. Heating is then carried out for 24 hours at 90° C. When the reaction is complete, the reaction mixture is poured into saturated NaHCO$_3$ solution (300 ml), the phases are separated, and the organic phase is washed with saturated NaHCO$_3$ solution until neutral. The organic phase is then dried over Na$_2$SO$_4$, filtered off and concentrated in a rotary evaporator. 195.4 g of crude product are obtained, the two isomers (IXa) and (IXb) wherein $R^1$=H being formed in a ratio of 3:1 and in an overall purity of 66.5%. The resulting crude product is used in the next step without being purified further. For structure determination by means of spectroscopy, a small sample of the crude product is purified by flash chromatography (cyclohexane/EtOAc=10:1, $R_f$=0.22).

The mass spectroscopic data relate to (IXa wherein $R^1$=H).

MS: m/z (%)=41 ($C_3H_5^+$, 82), 55 ($C_4H_7^+$, 43), 67 ($C_5H_7^+$, 43), 79 ($C_6H_7^+$, 75), 91 ($C_7H_7^+$, 100), 105 ($C_8H_9^+$, 67), 119 ($C_9H_{11}^+$, 60), 148 ($M^+$—$C_4H_6O$, 56), 175 ($M^+$—$C_3H_7^+$, 73), 203 ($M^+$—$CH_3$), 218 ($M^+$, 35).

Odour: intense sandalwood note, beautiful naturalness.

3.2 [4-(2,2,3-Trimethyl-cyclopent-3-enyl)-cyclohex-3-enyl]-methanol (Ia wherein $R^1$ and $R^2$=H)/[3-(2,2,3-trimethyl-cyclopent-3-enyl)-cyclohex-3-enyl]-methanol (Ib wherein $R^1$ and $R^2$=H)

To a suspension of lithium aluminium hydride (10.16 g, 0.27 mol.) in diethyl ether (400 ml) there is added dropwise the aldehyde (Ia/Ib=3:1, wherein $R^1$ and $R^2$=H, 178.0 g, 0.54 mol., 66.5% purity), dissolved in diethyl ether (150 ml), in such a manner that the diethyl ether boils slightly. When the addition is complete, stirring is carried out for 30 minutes before n-hexane (150 ml), water (150 ml) and 15% NaOH (100 ml) are added in succession. The resulting precipitate is filtered off with suction, the phases are separated, and the aqueous phase is extracted three times with diethyl ether (250 ml each time). The combined organic phases are dried over $Na_2SO_4$, filtered off and concentrated in a rotary evaporator. 151.8 g of crude product are obtained in 68% purity. Subsequent vacuum distillation on a 30 cm packed column (b.p.: 92-94° C., 0.07 mbar) yields the desired sandalwood fragrance (Ia/Ib=3:1, wherein $R^1$ and $R^2$=H) in 98% purity.

The spectroscopic data relate to (Ia wherein $R^1$ and $R^2$=H).

$^1$H-NMR (400 MHz, $CDCl_3$): δ (ppm)=0.74 (s, 3H), 1.05 (s, 3H), 1.18-1.38 (m, 2H), 1.59 (td, J=2.2, 1.6 Hz, 3H), 1.72-1.86 (m, 3H), 1.91-2.05 (m, 1H), 2.06-2.22 (m, 3H), 2.25-2.37 (m, 1H), 2.43 (t, J=8.3 Hz, 1H), 3.49-3.59 (m, 2H), 5.24-5.28 (m, 1H), 5.46-5.50 (m, 1H).

$^{13}$C-NMR (100 MHz, $CDCl_3$): δ (ppm)=12.7, 20.7, 25.9, 26.9, 27.7, 28.9, 32.5, 36.6, 48.2, 57.6, 67.8, 121.5, 121.6, 138.1, 147.3.

Odour: beautiful sandalwood note with musky aspects.

EXAMPLE 4

1-[4-(2,2,3-Trimethyl-cyclopent-3-enyl)-cyclohex-3-enyl]-ethanol (Ia wherein $R^1$=—$CH_3$ and $R^2$=H)

4.1 6-(2,2,3-Trimethyl-cyclopent-3-enyl)-1-oxa-spiro[2.5]oct-5-ene (XIV)

Trimethylsulfoxonium iodide (4.78 g, 21.63 mmol.) is added in portions to a suspension of sodium hydride (60% in mineral oil, 1.00 g, 25.54 mmol.) in DMSO (10 ml). Stirring is carried out for 30 minutes before 4-(2,2,3-trimethyl-cyclopent-3-enyl)-cyclohex-3-enone (XIII, see U.S. Pat. No. 5,189,013, 2.78 g, 13.64 mmol.), dissolved in DMSO (10 ml), is added. When the addition is complete, stirring is continued for a further 30 minutes, and then the reaction solution is poured onto ice (25 ml). The mixture is diluted with diethyl ether (50 ml), the phases are separated, and the aqueous phase is extracted three times with diethyl ether (50 ml each time). The combined organic phases are washed once with saturated NaCl solution before being dried over $Na_2SO_4$, filtered off and concentrated in a rotary evaporator. 3.08 g of crude product are obtained, which is then purified by flash chromatography (cyclohexane/EtOAc=20:1, $R_f$=0.22). 2.21 g of a colourless oil are obtained.

$^1$H-NMR (400 MHz, $CDCl_3$): δ (ppm)=0.78 (s, 3H), 1.06 (s, 3H), 1.51-1.59 (m, 1H), 1.60 (td, J=2.4, 1.7 Hz, 3H), 1.72-1.84 (m, 1H), 1.98-2.54 (m, 7H), 2.68-2.72 (m, 2H), 5.25-5.28 (m, 1H), 5.47-5.51 (m, 1H).

$^{13}$C-NMR (100 MHz, $CDCl_3$): δ (ppm)=12.7, 20.9, 26.8, 27.6, 29.7, 32.8, 33.0, 48.3, 53.9, 57.2, 57.5, 120.4, 121.5, 138.5, 147.3.

4.2 4-(2,2,3-Trimethyl-cyclopent-3-enyl)-cyclohex-3-enecarbaldehyde (IXa wherein $R^2$=H)

6-(2,2,3-Trimethyl-cyclopent-3-enyl)-1-oxa-spiro[2.5]oct-5-ene (XIV, 2.72 g, 12.5 mmol.), dissolved in toluene (5 ml), are added dropwise to a solution of $BF_3.OEt_2$ (1.7 ml) in toluene (20 ml). After 2 hours, the reaction solution is poured onto ice (10 ml), then the phases are separated and the organic phase is washed once with saturated NaCl solution. The organic phase is then dried over $Na_2SO_4$, filtered off and concentrated in a rotary evaporator. 2.07 g of crude product having a purity of 83% are obtained, which is used in the next step without being purified further.

The mass spectroscopic data correspond to those of Example 3.1.

Odour: very intense, natural sandalwood note.

4.3 1-[4-(2,2,3-Trimethyl-cyclopent-3-enyl)-cyclohex-3-enyl]-ethanol (Ia wherein $R^1$=—$CH_3$ and $R^2$=H)

To a 3M methylmagnesium chloride solution in THF (3.33 ml, 10.00 mmol.) there is added dropwise (IXa) wherein $R^2$=H (2.00 g, 7.60 mmol.), dissolved in diethyl ether (10 ml), in such a manner that the temperature does not exceed 35° C. When the dropwise addition is complete, stirring is carried out for one hour at room temperature. When the reaction is complete, the reaction solution is poured into cold $NH_4Cl$ solution (10 ml), the phases are separated, and the aqueous phase is extracted twice with diethyl ether (20 ml each time). The combined organic phases are washed once with saturated $NaHCO_3$ solution and saturated NaCl solution before being dried over $Na_2SO_4$, filtered off and concentrated in a rotary evaporator. 1.95 g of crude product are obtained, which is purified by flash chromatography (cyclohexane/EtOAc=25:1, $R_f$=0.22), so that (Ia) wherein $R^1$=—$CH_3$ and $R^2$=H is obtained.

The spectroscopic data and the odour correspond to those of Example 1.3 for (Ia) wherein $R^1$=—$CH_3$ and $R^2$=H.

EXAMPLE 5

Perfume Oil Composition

The perfume oil described hereinbelow can be used to perfume various cosmetic products, in particular for foam bath and shampoo.

Composition:

| Ingredients | Parts by weight |
| --- | --- |
| 1. Vertocitral 10% in DPG | 6.0 |
| 2. Bergamot oil pure | 15.0 |
| 3. Linalyl acetate | 30.0 |
| 4. Citral Nat. | 0.3 |
| 5. Aldehyde C14 so-called | 1.0 |
| 6. Decalactone gamma | 1.2 |
| 7. Linalool | 18.0 |
| 8. Citronellol 950 | 0.6 |
| 9. Geraniol supra. | 0.6 |
| 10. Geranyl acetate Pure | 0.3 |
| 11. Neryl acetate 10% in DPG | 4.0 |
| 12. Damascone Alpha | 0.4 |
| 13. Hedion HC/30 | 280.0 |
| 14. Veloutone 10% in DPG | 1.0 |
| 15. Isoeugenol acetate | 2.0 |
| 16. Heliotropin | 26.0 |
| 17. Ethylvanillin | 0.9 |
| 18. Vanillin | 17.0 |
| 19. Iso E Super | 140.0 |
| 20. Sandranol | 70.0 |
| 21. Teak Base | 50.0 |
| 22. Cetalox | 0.6 |
| 23. Ethylene brassylate | 22.0 |
| 24. Globalide | 55.0 |
| 25. Galaxolid 50% in IPM | 140.0 |
| 26. Dipropylene glycol | 48.1 |

DPG = dipropylene glycol; IPM = isopropyl myristate

The addition of 70 parts by weight [1-[4-(2,2,3-trimethyl-cyclopent-3-enyl)-cyclohex-3-enyl]-ethanol/1-[3-(2,2,3-tri-methyl-cyclopent-3-enyl)-cyclohex-3-enyl]-ethanol in a ratio of ~3:1 results in a clearly perceptible harmonisation of the flowery-vanilla-like core note. In addition, the intense soft sandalwood note, reminiscent of β-santalol, imparts to the present composition outstanding radiance, coupled with a tremendous spatial effect and increased adhesion. The valuable nature of [1-[4-(2,2,3-trimethyl-cyclopent-3-enyl)-cyclohex-3-enyl]-ethanol/1-[3-(2,2,3-trimethyl-cyclopent-3-enyl)-cyclohex-3-enyl]-ethanol in a ratio of ~3:1 is particularly evident.

The invention claimed is:

1. Compound of formula (Ia) or (Ib)

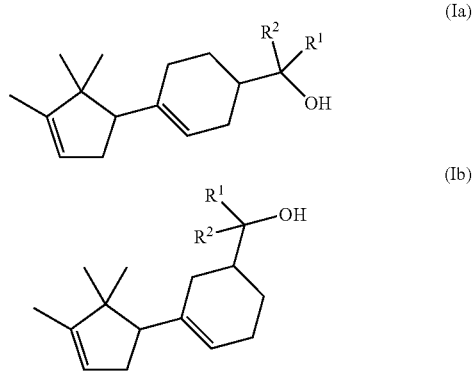

wherein in each of the formulae (Ia) and (Ib) $R^1$ and $R^2$, independently of one another, are H or $CH_3$.

2. Compound according to claim 1, wherein the compound is present in the form of
  (a) a pure optically active enantiomer,
  (b) a racemic mixture of different enantiomers of the diastereoisomeric enantiomer pairs, or
  (c) an optically active mixture of different enantiomers.

3. Compound according to claim 1, wherein:
  $R^1$ is $CH_3$, and
  $R^2$ is H.

4. Mixture comprising a compound of formula (Ia) and a compound of formula (Ib)

wherein in each of the formulae (Ia) and (Ib) $R^1$ and $R^2$, independently of one another, are H or $CH_3$.

5. Mixture according to claim 4, $R^1$ and $R^2$ in the compound of formula (Ia) are the same as in the compound of formula (Ib).

6. Mixture according to claim 5, comprising or wherein both in the compound of formula (Ia) and in the compound of formula (Ib)
  $R^1$ is $CH_3$, and
  $R^2$ is H.

7. Fragrance composition having a sandalwood odour, comprising a compound according to claim 1.

8. Fragrance composition according to claim 7 further comprising a carrier or substrate which is in direct contact with said compound.

9. Process for the preparation of a compound according to claim 1, comprising:
  reducing a compound of formula (IXa) or (IXb)

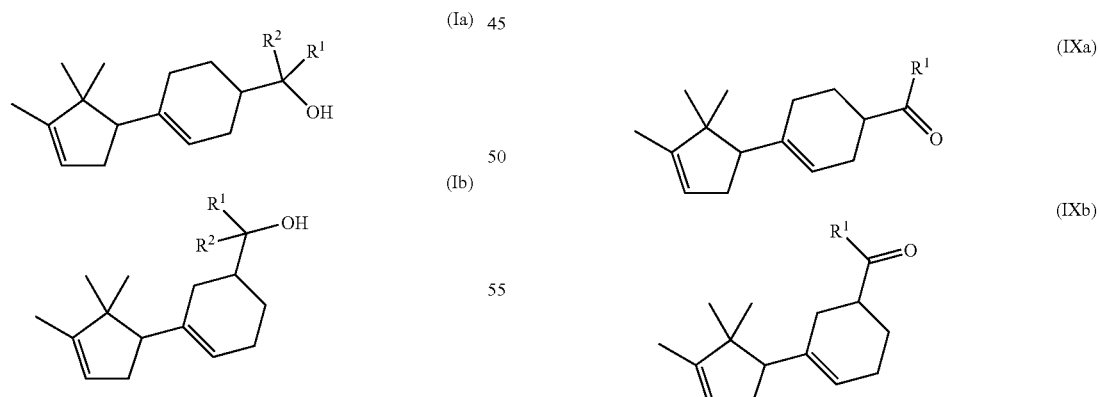

wherein $R^1$ represents H or $CH_3$, to form a compound according to claim 1 wherein $R^2$ is H.

10. Process according to claim 9 further comprising methylating said compound by nucleophilic addition of an organometallic compound of methyl anion nature to said compound to form a compound wherein $R^2$ is $CH_3$.

11. Process for the preparation of a compound of formula (Ia)

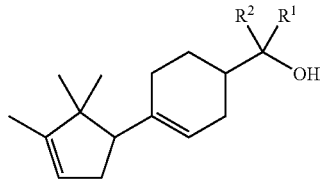
(Ia)

wherein
$R^1$ represents H or $CH_3$, and
$R^2$ represents H, comprising the following steps:
forming an aldehyde of formula (IXa) wherein $R^2$=H by an epoxide ring-opening reaction of a compound of formula (XIV) and

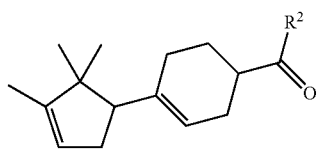
(IXa)

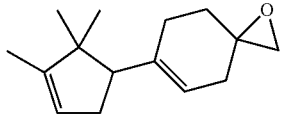
(XIV)

reducing said aldehyde of formula (IXa) to form a compound of formula (Ia) wherein $R^1$, $R^2$=H, or
methylating said aldehyde of formula (IXa) by nucleophilic addition of an organometallic compound of methyl anion nature to the aldehyde, to form said compound of formula (Ia) wherein $R^1$=$CH_3$, and $R^2$=H.

12. Method of producing, enhancing or modifying a sandalwood odour in a formulation, comprising the following steps:
mixing one or more compounds according to claim 1 with said formulation in an amount that is sufficient (a) to produce a sandalwood odour in the resulting mixture, (b) to enhance an existing sandalwood odour in said formulation.

* * * * *